(12) United States Patent
Bratchenia et al.

(10) Patent No.: US 9,999,784 B2
(45) Date of Patent: Jun. 19, 2018

(54) SKIN TREATMENT SYSTEM AND METHOD

(71) Applicant: KONINKLIJKE PHILIPS N.V., Eindhoven (NL)

(72) Inventors: Aliaksandr Bratchenia, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 367 days.

(21) Appl. No.: 14/397,884

(22) PCT Filed: Jun. 25, 2013

(86) PCT No.: PCT/IB2013/055196
§ 371 (c)(1),
(2) Date: Oct. 30, 2014

(87) PCT Pub. No.: WO2014/006535
PCT Pub. Date: Jan. 9, 2014

(65) Prior Publication Data
US 2015/0133848 A1    May 14, 2015

Related U.S. Application Data

(60) Provisional application No. 61/668,103, filed on Jul. 5, 2012.

(51) Int. Cl.
*A61N 5/06*    (2006.01)
*A61B 18/20*    (2006.01)
(Continued)

(52) U.S. Cl.
CPC ............ *A61N 5/062* (2013.01); *A61B 18/203* (2013.01); *A61B 18/26* (2013.01); *A61M 5/14248* (2013.01); *A61M 37/00* (2013.01); *A61N 5/0616* (2013.01); *A61B 2018/0047* (2013.01); *A61B 2018/00452* (2013.01);
(Continued)

(58) Field of Classification Search
CPC .............. A61M 5/2053; A61M 5/2046; A61M 2037/0007; A61M 5/30; A61N 5/062; A61B 18/26; A61B 2018/263
See application file for complete search history.

(56) References Cited

U.S. PATENT DOCUMENTS 5,713,845 A    2/1998    Tankovich
6,777,642 B2 *  8/2004    Song ..................... B08B 7/0042
                                                                 219/121.68
(Continued)

FOREIGN PATENT DOCUMENTS

DE    10144102 A1    3/2003
EP    2764884 A1    8/2014
(Continued)

OTHER PUBLICATIONS

Mi-Ae Park, "Er:YAG laser pulse for small-dose splashback-free microjet transdermal drug delivery" Optics Letters, Sep. 15, 2012, vol. 37, Issue 18, pp. 3894-3896.

*Primary Examiner* — Nathan R Price
*Assistant Examiner* — Weng Lee

(57) ABSTRACT

A system (101) for treatment of an epithelial tissue layer (3) is provided. The system comprises a reservoir (107), for containing an amount of a flowable medium, arranged to enable the medium, when contained in the reservoir, to be in contact with a surface (5) of the epithelial tissue layer, a light source (109) for generating a laser beam (11) during at least a predetermined pulse time, and an optical system for focusing the laser beam into a focal spot (15), and for positioning the focal spot in a target position. The target position of the focal spot is within the reservoir and within the medium, when contained in the reservoir, and the dimension of the focal spot and the power of the generated laser beam are such that, in the focal spot, the laser beam has a power density, which is above the characteristic threshold value for the medium, above which, for the predetermined pulse time, a laser induced optical breakdown event occurs in the medium. A method for treatment of an epithelial tissue layer is also provided.

20 Claims, 4 Drawing Sheets

(51) Int. Cl.
    *A61M 37/00* (2006.01)
    *A61M 5/142* (2006.01)
    *A61B 18/26* (2006.01)
    A61M 5/30 (2006.01)
    A61B 18/00 (2006.01)

(52) U.S. Cl.
    CPC ............ *A61B 2018/00577* (2013.01); *A61B 2018/202* (2013.01); *A61B 2018/263* (2013.01); *A61B 2018/266* (2013.01); *A61M 2005/3022* (2013.01); *A61M 2037/0007* (2013.01); *A61M 2205/058* (2013.01)

(56) References Cited

U.S. PATENT DOCUMENTS

| | | | |
|---|---|---|---|
| 2001/0007079 | A1 | 7/2001 | Chernoff |
| 2002/0045911 | A1* | 4/2002 | Fletcher ............ A61B 17/3203 606/167 |
| 2002/0062101 | A1 | 5/2002 | Kollias |
| 2007/0239232 | A1 | 10/2007 | Kurtz |
| 2009/0000665 | A1* | 1/2009 | Oshemkov ............ A61B 18/26 137/13 |
| 2009/0299266 | A1 | 12/2009 | Bernabei |
| 2011/0230826 | A1* | 9/2011 | Yoh ..................... A61M 5/30 604/70 |
| 2011/0257584 | A1 | 10/2011 | Altshuler |
| 2013/0066263 | A1 | 3/2013 | Yoh |

FOREIGN PATENT DOCUMENTS

| | | |
|---|---|---|
| JP | 2006325700 A | 7/2006 |
| WO | 9641657 A1 | 12/1996 |
| WO | 0071038 A1 | 11/2000 |
| WO | 2008001284 A2 | 1/2008 |

* cited by examiner

SKIN TREATMENT SYSTEM AND METHOD

This application is the U.S. National Phase application under 35 U.S.C. § 371 of International Application No. PCT/IB2013/055196, filed on Jun. 25, 2013, which claims the benefit of U.S. Provisional Application No. 61/668,103 filed on Jul. 5, 2012. These applications are hereby incorporated by reference herein.

TECHNICAL FIELD

The present disclosure relates to epithelial tissue treatment, in particular skin treatment. More in particular, the present disclosure relates to improvements in transport of topical formulations into the skin, improvements in inducing skin rejuvenation and/or improvements in healing of skin.

BACKGROUND

Mammalian epithelial tissue, in particular skin tissue, forms a barrier between the mammalian body and the outside world. A healthy and youthful looking skin is generally sought after and there is a continuous demand for improvements in the field of skin care and/or skin rejuvenation, both for curative and cosmetic purposes. The presently provided system and method address such demands.

Human skin tissue comprises dermis and epidermis layers, wherein the stratum corneum is the outermost layer of the epidermis. Suitable techniques for treatment of epithelial tissue may comprise application of one or more topical formulations, and, for particular treatments, topically applied formulations are used, which should cross the stratum corneum and/or lower epithelial layers.

A manner to provide increased transport of topical formulations into the skin and across the stratum corneum is known from US 2002/0062101, which discloses a method and an apparatus for delivering compounds through epithelial cell layers, using impulse transients. The method involves applying a compound to, e.g., the stratum corneum of a patient and then inducing impulse transients to create transient increases in the permeability of epithelial tissue, thereby facilitating delivery of the compound across the epithelial cell layer. The impulse transient can be generated by exposing a target material to a pulsed laser beam and ablating or rapidly heating the target material.

This known method is critically dependent on the mechanical coupling between the target material and the medium, in which the impulse transient is to be induced. Hence, the amount of the compound that is delivered through the epithelial cell layer is neither accurately known nor reliable and/or controllable. Furthermore, ablation of the target material unavoidably produces debris, which may contaminate the apparatus and/or the subject being treated.

Therefore, improvements in transporting topical formulations into the skin are particularly desired.

SUMMARY

A system for treatment of an epithelial tissue layer according to the appended claims is hereby provided. The system comprises a reservoir, for containing an amount of a flowable medium, arranged to enable the medium, when contained in the reservoir, to be in contact with a surface of the epithelial tissue layer, a light source for generating a laser beam during at least a predetermined pulse time, and an optical system for focusing the laser beam into a focal spot and for positioning the focal spot in a target position. The target position of the focal spot is within the reservoir and within the medium, when contained in the reservoir. A dimension of the focal spot and a power of the generated laser beam are such that, in the focal spot, the laser beam has a power density which is above a characteristic threshold value for the medium, above which, for the predetermined pulse time, a laser-induced optical breakdown (LIOB) event occurs in the medium.

Thus, the system is configured to deliver at least one pulse of light from the light source into the reservoir and to generate a LIOB event within the medium, when contained in the reservoir, causing an impulse transient within the medium to affect the surface of the epithelial tissue layer. The impulse transient may comprise a compression wave having a continuous rise time, a shock wave having a discontinuous rise time, a series of compression or shock waves and/or a fluid jet. Shock waves, series of shock waves and/or jets may be produced by suitable values of the dimension of the focal spot, the power of the generated laser beam, the target position in the medium, and the viscosity of the medium, chosen such that the LIOB event causes formation of a bubble in the medium, which may exhibit cavitation, suffer (repeated) collapse, and/or exhibit jet formation.

The system facilitates the creation of an impulse transient directly in the medium, so that the impulse transient and its effects on the epithelial tissue layer may be provided reliably and may be controlled. The impact causes the epithelial tissue layer to become locally in disarray and/or to be damaged, so that its barrier function is corrupted and the substance may be able to pass through (more easily or at all).

In general, laser-induced optical breakdown (LIOB) occurs in media that are transparent or semi-transparent to the wavelength of the used laser beam, when the power density of the laser beam in the focal spot exceeds a threshold value which is characteristic of the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. The LIOB phenomenon results in a number of mechanical effects, such as cavitation and the generation of shock waves, which affect the medium in the vicinity of the position of the LIOB phenomenon and which can be used to disrupt (at least the surface of) the epithelial tissue layer.

Said threshold value is dependent on the pulse time of the laser beam. In particular, the threshold value of the required power density (in $W/cm^2$) decreases when the pulse time increases. For suitable media it appears that, in order to achieve mechanical effects as a result of the LIOB phenomenon which are sufficiently effective so as to cause significant damage, a pulse time in the order of, for example, 10 ns suffices. For such a value of the pulse time, the threshold value of the power density of the laser beam in the focal spot may be in the order of $2*10^{10}$ $W/cm^2$. For the described pulse time and with a sufficiently small focal spot size obtained, for example, by means of a lens or a focusing system having a sufficiently large numerical aperture, this threshold value can be achieved with a total pulse energy of only a few tenths of a mJ, which may be provided with relatively low-cost lasers. As an additional advantage, the so-called resonant plasma absorption may occur in the focal spot, which means that, as a result of the LIOB phenomenon, substantially all energy of the laser beam is absorbed in the focal spot. As a result, systems and methods provided herewith can exhibit a relatively high efficiency.

Preferably, the medium is biocompatible for introduction into the body. The medium may be a gel or a liquid at normal operating conditions (e.g., at room temperature or at mammalian body or skin temperature). This facilitates control over the impulse transient and allows the creation of a plurality of LIOB events under substantially identical conditions, since the medium that has been affected by a LIOB event may be replaced by material flowing to the affected site from another portion of the amount of medium so that effectively the medium at the original target position is restored. Note that this overcomes a drawback of LIOB in or near a solid object which suffers from ablation or a different form of destruction, e.g. as in US 2002/0062101, wherein inherently the solid object alters its geometry so that subsequent light pulses may produce different effects.

The medium may comprise a therapeutic substance, wherein delivery of the substance into the epithelial tissue layer is facilitated by the force of the impulse transient. Also, or alternatively, the substance may be provided as a separate substance on the epithelial tissue layer, e.g. in a topical formulation, which can be applied either after delivery of the light pulse(s) or before that, wherein in the latter case the medium may be in contact with the surface of the epithelial tissue layer via the substance and/or the topical formulation. However, it is possible that the topical formulation comprises the therapeutic substance as a mixture with the same material as the medium for the LIOB event.

A fluid jet can occur in the case of low viscosity liquid media, e.g. water, alcohol etc. A jet may be caused by formation and implosion of a cavitation bubble, in particular formed within the medium near a boundary with a substantially rigid material relative to the medium supporting the cavitation bubble, such as provided by human skin relative to a low-viscosity fluid. Typically, fluid jets are produced by cavitation bubbles created within the medium at distances from such boundaries of the same order of magnitude as the maximum size of the cavitation bubble before its implosion, which is related to the energy of the LIOB event causing formation of the cavitation bubble and the properties of the fluid supporting the cavitation bubble, as known in the art. A LIOB event may be generated in viscous media like creams. To sustain and/or promote jet formation, the medium may preferably be a liquid with a viscosity of about 100 centiPoise or below, such as light oils, preferably below about 10 centiPoise or below, e.g. at about the viscosity of whole human blood; in some cases the medium may have a viscosity of about 2 centiPoise or below, e.g. at about the viscosity of water or even lower such as about 0.1 centiPoise in the case of fluids based on particular spirits and/or alcohols.

It has been found that such a cavitational fluid jet can penetrate into/through a mammalian epithelial tissue layer, in particular skin tissue, and that it may be used to create cavities and/or open channels into and/or through the epithelial tissue layer. Further, a jet provides mass transfer by directly injecting into the tissue the material that forms the jet. The penetration depth of a fluid jet depends on its volume and impulse, which in turn depend on factors such as the pressure of the medium, the flow characteristics of the medium, the size and pressure of the cavitation bubble, causing the jet, and the distance between the onset of the jet (typically, the position at which the cavitation bubble rear wall ruptures upon bubble collapse and into the interior volume of the bubble) and the jet target (i.e. the epithelial tissue layer), and the amount of medium available for forming and sustaining the jet. The volume injected in the epithelial tissue may be controlled by creation of a series of successive jets at substantially the same location.

Further, jets tend to produce very small size tissue damage, which is suitable for causing tissue rejuvenation by inciting a tissue healing response of the treated tissue. Injection of a cooled medium, e.g. cold water, may soothe feelings of irritation which may otherwise accompany epithelial tissue treatment comprising damaging of the tissue.

The light source comprises a laser, which provides benefits like controllable optical power, coherent beam formation and low spectral bandwidth, which facilitate reliability, steering and focusing the light to a small spot, and, respectively, predictable transmission and/or absorption in optics and/or the medium.

The light source may be configured to emit a laser beam at a wavelength in a range of about 250-3000 nm, where suitable lasers are available, and which wavelength range is appropriate for causing LIOB events in readily available biocompatible fluid media. Preferably, the wavelength is in a range of about 800-1350 nm, which reduces the danger of harming human epithelial tissue, like skin, by light that has passed unabsorbed through the reservoir and the medium. Most preferably the wavelength is in a range of about 900-1100 nm, where the penetration depth of human skin is highest, preventing accidental power build-up within the skin.

Advantageously, the laser is a solid state laser, which may provide, inter alia, large optical power in a small package while the required input power is low compared to other types of lasers. Series of suitable high power, short duration laser pulses may be provided in a controlled manner by a Q-switched laser.

In the system, in operation, the target position may be located at a distance d between 0 mm and 10 mm from the surface of the epithelial tissue layer. At such separations, the effects of a LIOB event may be provided most reliably and controllably. At relatively short distances from the surface of the epithelial tissue layer, e.g. below about 3 mm from a skin surface, the effects on the tissue layer become more pronounced and a formed jet may penetrate the surface of the layer. Also, the system may have a user-friendly size.

The system may advantageously be configured such that, in use, the LIOB event in the medium causes a jet of the medium, which propagates in a direction towards the epithelial tissue layer, as set out above. In particular, the dimension of the focal spot, the power of the generated laser beam, the target position in the medium, and the viscosity of the medium are controlled such that the LIOB event in the medium causes formation of a jet of the medium propagating in a direction towards the epithelial tissue layer.

To increase the versatility of the system, the system may comprise a controller for controlling operation of the light source and/or the optical system so as to control at least one of the following parameters: light pulse power, light pulse duration and light pulse repetition rate of the light source and/or the target position of the focal spot with respect to the reservoir and/or, when in use, with respect to the surface of the epithelial tissue layer. The light pulse power, light pulse duration and light pulse repetition rate of the light source may be controlled to provide various impulse transients and/or various sequences thereof, in accordance with one or more desired treatments.

Position control of the target position of the focal spot may comprise control of the target position with respect to the axial and/or lateral position of the focal spot with respect to the propagation direction of the laser beam and relative to the reservoir and/or in particular, in use, relative to (the surface of) the epithelial tissue layer (surface). Axial position control relates to determining the separation between the target position and the epithelial tissue layer, which may be used to cause different types of impulse transients, e.g. the rising and falling characteristics of a shock wave, formation of a jet etc. Lateral position determination may relate to positioning one or more focal positions in desired positions distributed over the epithelial tissue layer, e.g. facilitating treating several adjacent locations. The control may be constant or variable between subsequent pulses so as to maintain a parameter setting or rather to change between different parameter settings.

The optical system may comprise one or more suitable optical elements such as mirrors, lenses, prisms, beam splitters, diaphragms, optical switches, shutters, etc.

In an embodiment, the reservoir comprises a window and/or one or more lenses to transmit light from the light source into the reservoir and, when the medium is contained in the reservoir, into the medium. Thus, (part of) the reservoir may form a part of the optical system. This facilitates focusing the light into the medium with a large numerical aperture, leading to a tight focus and facilitating providing a substantially spherical cavitation bubble.

The system may comprise a supply system to provide an amount of the medium to the reservoir, e.g. from a storage container. This is useful in particular for operation of the system with a liquid medium having a low to medium-high viscosity like water, an alcohol, cream or oil. The supply system may comprise one or more nozzles connected to the reservoir and/or a metering system to provide one or more metered doses of the medium into the reservoir.

In a preferred system, the reservoir is releasably coupled with the light source and/or with the optical system, e.g. it is attached to a housing portion of the system by means of a suitable connector system comprising one or more mated connectors and counter connectors, so that (the reservoir of) the system can be adapted to properties of the light source and/or the medium, and/or exchanged for maintenance and/or repair. The connector system may define one or more particular relative positions of the reservoir relative to (the remainder of) the optical system, e.g. to ensure a particular target position of the focal spot within the reservoir. Further, a reservoir may be provided as a one-waycartridge that may be pre-filled with a medium, possibly comprising a substance to be delivered through an epithelial tissue layer.

The system may comprise one or more detectors configured to detect the presence of a reservoir and/or a target tissue at a particular distance from a portion of the system from which the laser beam may be emitted and/or configured to detect particular reservoir properties, such as size indications and/or indications of properties of the reservoir and/or the medium (to be) contained in the reservoir, which may be used for operation control of the system. Such detectors may be mechanical, electrical, magnetic and/or optical and/or operate in conjunction with suitable structures on the reservoir.

Further, a method for treatment of an epithelial tissue layer is provided herewith. The method comprises the steps of providing the system of any one of the embodiments disclosed herein, arranging the reservoir comprising an amount of a flowable medium on a surface portion of the epithelial tissue layer, the medium being able to be in contact with a surface of the epithelial tissue layer when it is contained in the reservoir; and generating a laser beam during at least the predetermined pulse time and focusing the generated laser beam into a focal spot in a target position within the medium. A dimension of the focal spot and a power of the generated laser beam are such that, in the focal spot, the laser beam has a power density which is above a characteristic threshold value for the medium, above which, for the predetermined pulse time, a laser induced optical breakdown event occurs in the medium.

Thus, the method amounts to delivering a pulse of light into the amount of medium, causing a LIOB event in the medium so as to cause an impulse transient within the medium in a direction toward the epithelial tissue layer.

As elucidated above, causing a LIOB event within the medium enables controlling the impulse transient, which may comprise causing a shock wave, a cavitation bubble and/or a jet of the medium which propagates in a direction toward the epithelial tissue layer for disrupting the epithelial tissue layer.

In the method, the laser-induced optical breakdown event in the medium may be controlled to cause a jet of the medium, which propagates in a direction towards the epithelial tissue layer. For example, the dimension and target position of the focal spot, the power of the generated laser beam and a viscosity of the medium may be such that the laser-induced optical breakdown event in the medium causes a jet of the medium, which propagates in a direction towards the epithelial tissue layer. Formation of a jet is preferred for increased reliability of disruption of the epithelial tissue layer.

The method may comprise injecting a portion of the medium into the epithelial tissue layer, e.g. for penetration of the epithelial tissue layer to damage it and incite rejuvenation of the tissue and/or for injection of the medium as a topical formulation.

The medium may be contained in a reservoir, wherein the medium is in fluid contact, preferably substantially in direct contact, with a surface of the epithelial tissue layer. A reservoir facilitates performing the method with a low-viscosity medium, e.g. to retain the medium in place and/or to prevent splashing and/or loss of pressure of the impulse transient. It may further increase hygiene.

The method may comprise repeating the step of generating a laser beam and causing a laser-induced optical breakdown event within the medium a plurality of times, wherein the target positions of at least some focal spots may differ from each other. Thus, a plurality of impulse transients within the medium are caused in a direction toward the epithelial tissue layer, e.g. for increasing duration, intensity, effect and/or spatial extent of the treatment.

Before or after the application of one or more impulse transients, a topical formulation may be applied on the treated epithelial tissue layer, which topical formulation may comprise one or more substances to be delivered through the treated epithelial tissue layer, possibly in addition to a substance present in the medium.

DETAILED DESCRIPTION OF EMBODIMENTS

Figure 1:
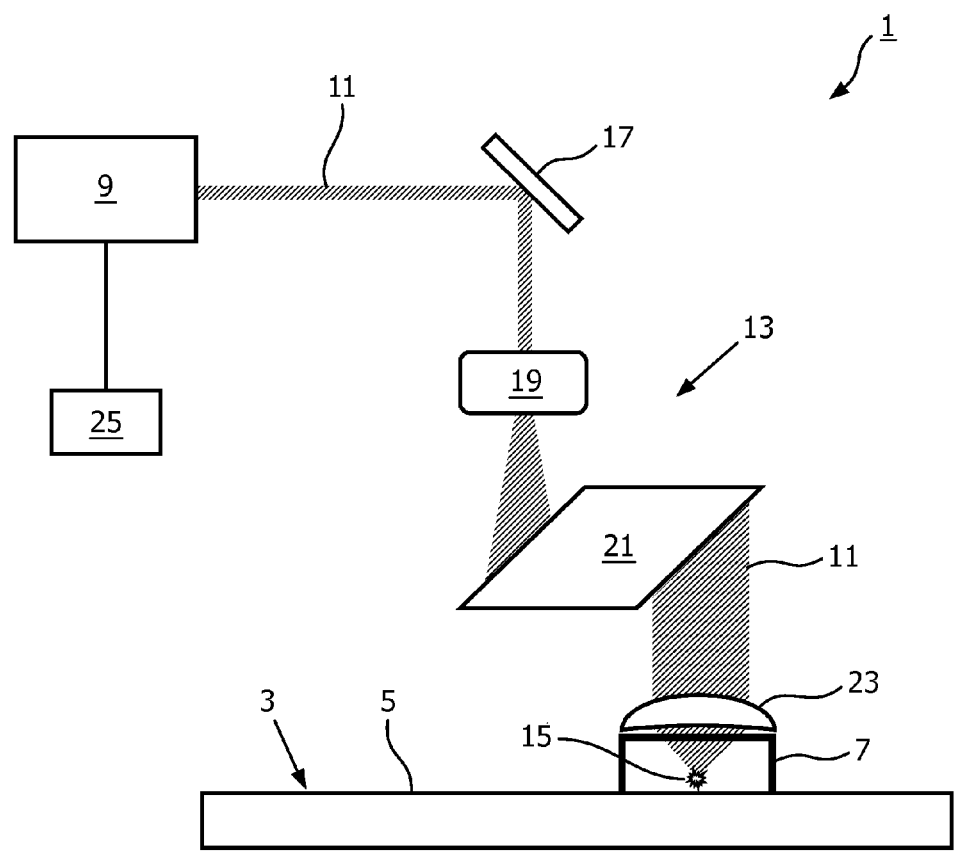
FIG. 1 indicates a step of a method for treatment of an epithelial tissue layer and a system for such a method.

It is noted that, in the drawings, like features may be identified with like reference signs. It is further noted that the drawings are schematic, not necessarily to scale, and that details that are not required for understanding the present invention may have been omitted. The terms "upward", "downward", "below", "above", and the like relate to the embodiments as oriented in the drawings. Further, elements that are at least substantially identical or that perform an at least substantially identical function are denoted by the same numeral, raised by 100, 200, etc., for different, shown embodiments.

FIG. 1 indicates a system 1 for treatment of an epithelial tissue layer 3, here a portion of skin tissue, having a surface 5. The system comprises a reservoir 7 containing an amount of a flowable medium. The reservoir 7 is generally cup-shaped with an open bottom and is arranged to enable the medium to be in contact with the surface 5 of the epithelial tissue layer 3. The system 1 further comprises a light source 9 for generating a laser beam 11 during at least a predetermined pulse time, and it comprises an optical system 13 for focusing the laser beam 11 into a focal spot 15 and for positioning the focal spot 15 in a target position within the reservoir 7, which is at least partly transparent to the light from the light source 9. The optical system 13 schematically indicated in FIG. 1 comprises a beam steering system 17, a beam shaping system 19, a beam scanning system 21 and a focusing system 23, which systems may comprise one or more mirrors, prisms, beam splitters, polarizers, optical fibers, lenses, apertures, shutters, etc. However, different optical systems with more, fewer and/or differently arranged optical sub-systems and/or elements may be suitably provided. At least part of the optical system 13 and/or the beam path of the laser beam 11 may be enclosed, e.g. for eye-safety, e.g. comprising opaque tubes and/or one or more optical fibers.

The light source 9 is configured to emit a predetermined number of laser pulses at a predetermined wavelength and with a predetermined pulse duration and repetition rate. The system 1 is configurable such that the target position of the focal spot 15 is within the reservoir 7 and within the medium, when contained in the reservoir 7, as indicated, and such that the dimension of the focal spot 15 and the power of the generated laser beam are such that, in the focal spot 15, the laser beam 11 has a power density, which is above the characteristic threshold value for the medium, above which, for the predetermined pulse time, a laser-induced optical breakdown event occurs in the medium.

The system 1 is configured such that the target position for the focal spot 15 is located at a distance between 0 mm and 10 mm from the surface 5 of the epithelial tissue layer 3, e.g. a distance in a range between about 300 and 900 micrometer from the surface 5 is found suitable for treating human skin.

The light source 9 is controllable with an optional controller 25, which may provide a user interface. Also, one or more (subsystems 17-23 of) the optical system 13 may be controllable with an optional controller (not shown), which may be integrated with a light source controller 25 to control one or more properties of the target position and/or the focal spot. A suitable controller may comprise a programmable memory and it may comprise one or more systems for programming the memory, possibly including one or more (connectors for) readers of data storage media and/or an internet connection. For example, for a first medium the system 1 may be configured to provide a first laser pulse power density according to the characteristic LIOB threshold value of the first medium, and for a second medium the system 1 may be configured to provide a second laser pulse power density according to the characteristic LIOB threshold value of the second medium, which first and second power densities may be determined by appropriate first and second pulse powers, pulse durations and/or laser beam focusing parameters, possibly also for further media. Laser beam focusing parameters may be determined by appropriate settings of a beam shaping and/or focusing system, e.g. by adjustment of the numerical aperture of the focusing system. Suitable values for the numerical aperture NA of the focusing system may be chosen from a range $0.05<NA<n_m$, wherein $n_m$ is the index of refraction of the medium for the laser wavelength, during operation.

A suitable light source comprises a Q-switched Nd:YAG laser emitting laser pulses at a wavelength of about 1064 nm with a pulse duration of about 5-10 ns, although other lasers, e.g. a Nd:Cr:Yag 3-level laser and/or diode lasers may be used as well.

Figure 2:
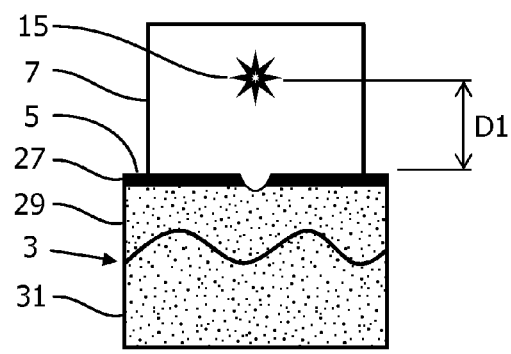
FIGS. 2-4 each indicate a step of a method for treatment of an epithelial tissue layer.
Figure 3:
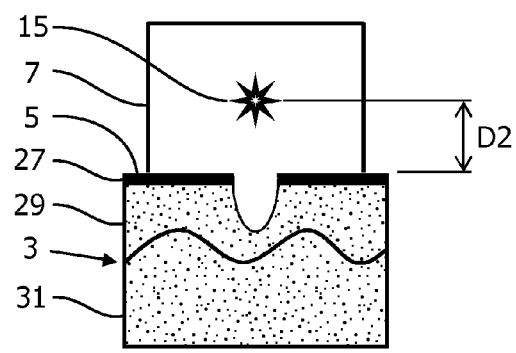
Figure 4:
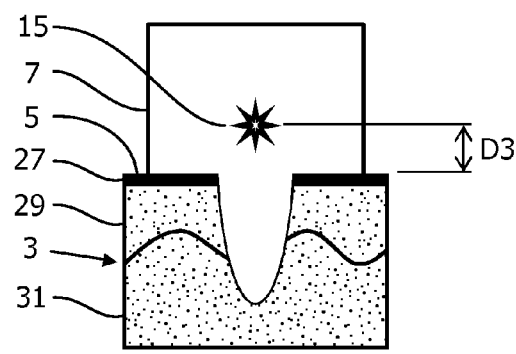

FIGS. 2-4 each show a step of a method for treatment of an epithelial tissue layer, and indicate a portion of skin 3 on which a reservoir 7 is placed. The skin 3 comprises the layers of stratum corneum 27 forming the surface layer, epidermis 29 and dermis 31, below which subdermal tissue extends (not shown). The reservoirs 7 are filled with a non-solid medium, e.g. selected from a group comprising water, PBS (phosphate buffered saline solution), oil, glycerol, fluorinated carbons, surfactants (polyethylene glycol/polypropylene glycol), alcohols, glucose (sugar) solutions, topicals (creams, gels, etc.). Upon focusing of a laser pulse into a focal spot with sufficient power density within the medium, e.g. a laser pulse of wavelength $\lambda=1064$ nm at a pulse duration of $\tau p=6$ ns and a pulse energy of $Ep=1$ mJ focused with a numerical aperture $NA=0.8$ in the medium, a LIOB event is created in the focal spot 15 at a distance from the stratum corneum 27.

FIGS. 2-4 indicate (the use of) LIOB events caused by focal spots, which are created in target positions at exemplary distances D1, D2 and D3 of about 0.75 mm, 0.6 mm and 0.4 mm, respectively, from the skin surface 5, but with otherwise identical conditions. The LIOB events in the medium result in a shock wave traveling towards the skin 3. In FIG. 2, the shock wave locally destroys the stratum corneum 27, in FIG. 3, the shock wave penetrates also into the epidermis 29 and in FIG. 4 the damage extends even into the dermis layer. After such penetration of the stratum corneum, an active substance can be readily absorbed by the skin from a topical formulation applied onto the skin surface, e.g. for curative and/or cosmetic purposes. Damage to the epidermis and/or dermis can incite a healing response of the skin which may comprise formation of new collagen and which may lead to tightening and/or other rejuvenation of the skin. The extent of the damage inflicted with the presently provided system and method may be controlled not only by the distance between the focal spot and the skin, but also by the power in the laser beam and/or the size of the focal spot. Further, providing a laser pulse train and/or creation of a bubble exhibiting repeated cavitation in the medium by a single LIOB event may provide a series of shock waves towards the skin 3 and yield an increased effect relative to a single pulse.

Figure 5A:
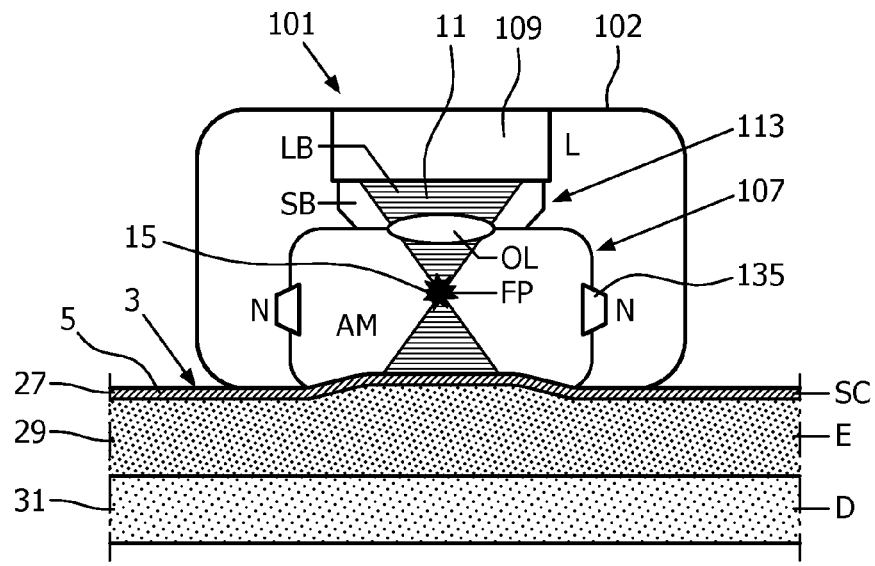
FIGS. 5(a)-5(d) indicate steps of a method for treatment of an epithelial tissue layer and a detail of a system for such a method.
Figure 5B:
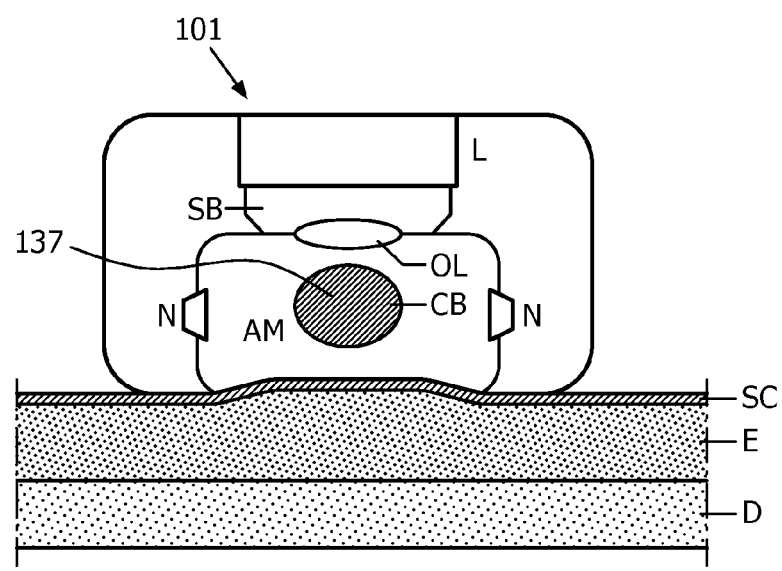
Figure 5C:
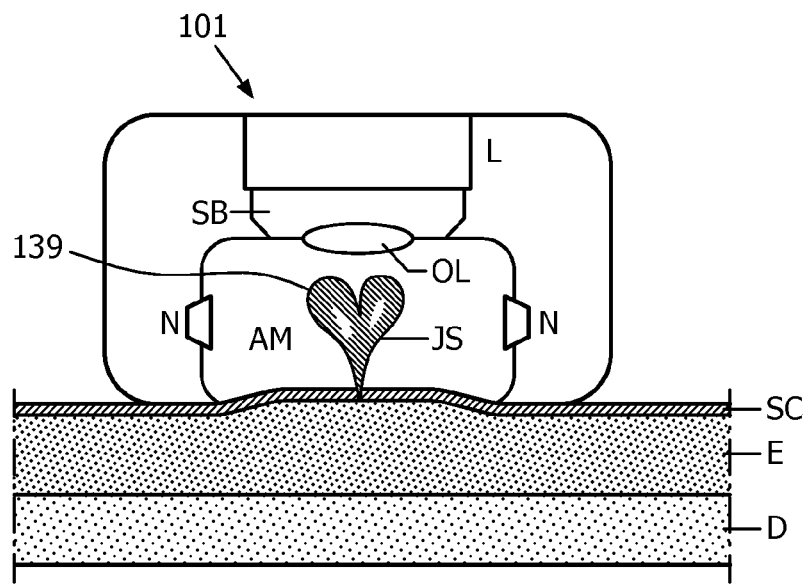
Figure 5D:
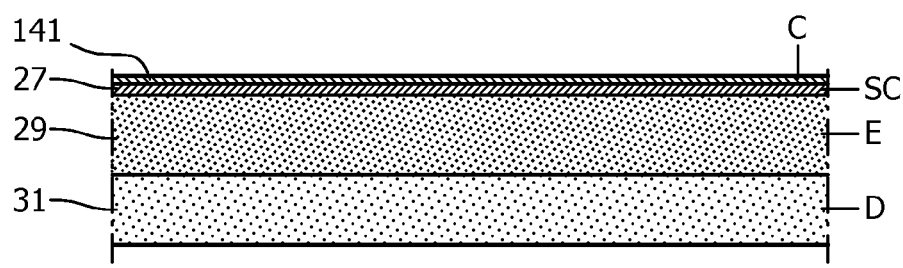

A particular method is disclosed in FIGS. 5(a)-5(d). FIGS. 5(a)-5(c) schematically show a portion of a system 101, comprising a housing 102. The system 101 comprises a reservoir 107, a laser 109 and an optical system 113, which here includes a lens 114 comprised in the reservoir 107. In this system 101, the reservoir 107 is provided with optional nozzles 135, which connect to an optional supply system (not shown) to provide an amount of the medium to the reservoir 107, e.g. said supply system comprising a reservoir and a pump. The system 101 is arranged on a portion of the surface 5 of the skin 3 of a subject to be treated. When the laser 109 is activated to provide a LIOB event at a target position in the medium close to the skin surface 5 (FIG. 5(*a*)), the LIOB event creates a cavitational bubble 137 (FIG. 5(*b*)) within the medium, which collapses and develops a liquid jet 139 (FIG. 5(*c*)) on the side of the bubble 137 remote from the skin. The jet 139 shoots through the collapsing bubble 137 in a direction towards the skin 3, thereby penetrating the opposite bubble wall. Dependent on the distance between the focal spot 115 and the skin surface 5, the jet 139 merely impinges on the skin surface 5, thereby causing a shock, or it penetrates through the stratum corneum 27 and possibly penetrates into the epidermis 29 or even into the dermis 31 (cf. FIGS. 2-4). After this, a topical formulation such as a cream 141 may be applied onto the treated portion (FIG. 5(*d*)).

In FIGS. 5(*a*)-5(*d*) different features are indicated by means of one or more letters: L—laser; LB—laser beam; SB—scanning block; OL—focusing optical element (e.g., lens); FP—focal point; AM aqueous medium ("aqueous" in the sense of: having a water-like viscosity) as an exemplary target medium; N—nozzle for target medium injection; CB—cavitational bubble; JS jet stream; SC stratum corneum; E epidermis; D dermis; C topical formulation (e.g., cream).

When penetrating into the skin 3, a jet 139 deposits an amount of the medium into the skin tissue, which may comprise a beneficial active substance. Media comprising active substances which may suitably be delivered locally and superficially into the skin tissue by a jet may be selected from, inter alia, vitamin A solutions, vitamin C solutions, vitamin E solutions, collagen production stimulants, alpha hydroxy acids, hydroquinone, niacinamide and/or kojic acid.

Topical substances could contain solutions of e.g. niacinamide for treatment of acne and for skin whitening, or retinaldehyde for wrinkle reduction. Alternatively, a solution of copper peptides could be used to accellerate a healing effect after treatment.

Typical jet volumes are in the range of nanoliters to microliters. By providing a plurality of jets, an increase of the total amount of medium that is injected is achieved; a plurality of jets may be provided in a single position in rapid succession, e.g. to inject a subsequent jet in a certain position before the skin can absorb a previously injected amount of medium at that position.

It is noted that one LIOB event may cause a rapid sequence of bubble formation and bubble collapse, which may comprise the formation of a series of jets. However, each cycle of bubble formation and bubble collapse, with or without jet formation, dissipates energy and the process is therefore self-terminating if it is not actively sustained. Overdosing may thus be prevented.

A reservoir 7, 107 may be exchangeable, e.g. to account for different optical qualities and/or laser wavelengths, (optical) aging of the reservoir and/or the medium contained therein, exchanging media, etc. Optionally, a reservoir may have a general cup-shape and may be made of a relatively rigid material having an opening therein, which is closed with a tear-away tab, a thin film or thin paraffin layer etc. to seal the reservoir containing an amount of a suitable, possibly low-viscosity medium, but which closure is readily meltable by the body heat of the subject to be treated and/or destroyed by (a shock generated by) the LIOB event without adverse effects in use. Also, different reservoirs may comprise particular lenses and/or lens arrays for providing different foci.

The method may be used for cosmetic and/or curative purposes, which may depend on the number of LIOB events caused per target position and/or the administration of one or more substances onto and/or into the tissue. For example, such a difference may be discernible in that up to about 5 LIOB events are generated for cosmetic purposes and about 10 or more LIOB events at or near one target position are generated for curative treatment.

The system may comprise a handheld portion, e.g. comprising the reservoir, which may comprise the light source. It is also conceivable that a handheld portion is connected to the light source via a laser beam transfer system.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for treatment of an epithelial tissue layer, the system comprising:
a reservoir containing, in operation, an amount of a flowable medium, arranged to enable the medium, when contained in the reservoir, to be in fluid contact with a surface of the epithelial tissue layer;
a light source for generating a laser beam during at least a predetermined pulse time, wherein the light source is external to the reservoir; and an optical system for focusing the laser beam into a focal spot, and for positioning the focal spot in a target position;
wherein the target position of the focal spot is within the reservoir and within the medium, when contained in the reservoir, and wherein a dimension of the focal spot and a power of the generated laser beam are such that, in the focal spot, the laser beam has a power density which is above a characteristic threshold value for the medium, above which, for the predetermined pulse time, a laser-induced optical breakdown event occurs in the medium.

2. The system of claim 1, wherein the light source is configured to emit a laser beam at a wavelength in a range of about 250-3000 nm, preferably in a range of about 800-1350 nm, most preferably in a range of about 900-1100 nm.

3. The system of claim 1, wherein, in operation, the target position is located at a distance in a range between 300 and 900 micrometer from the surface of the epithelial tissue layer.

4. The system of claim 1, wherein the system is configured such that, in use, the laser-induced optical breakdown event in the medium causes a jet of the medium, which propagates in a direction towards the epithelial tissue layer.

5. The system of claim 1, comprising a controller for controlling operation of the light source and/or the optical system so as to control at least one of a light pulse power, light pulse duration and light pulse repetition rate of the light source and/or the target position of the focal spot with respect to the reservoir and/or, when in use, with respect to the surface of the epithelial tissue layer.

6. The system of claim 1, wherein the system comprises an amount of the flowable medium in the reservoir.

7. The system of claim 1, wherein the system comprises a supply system to provide an amount of the medium to the reservoir.

8. The system of claim 7, wherein the system comprises an amount of the flowable medium in the supply system.

9. The system of claim 1, wherein the reservoir is releasably coupled with the light source and/or the optical system.

10. A method for treatment of an epithelial tissue layer, the method comprising the steps of:
   providing the system of any one of the preceding claims;
   arranging the reservoir, comprising an amount of a flowable medium, on a surface portion of the epithelial tissue layer, the medium being able to be in fluid contact with a surface of the epithelial tissue layer when it is contained in the reservoir; and
   generating a laser beam during at least the predetermined pulse time and focusing the generated laser beam into a focal spot in a target position within the medium;
   wherein a dimension of the focal spot and a power of the generated laser beam are such that, in the focal spot, the laser beam has a power density which is above a characteristic threshold value for the medium, above which, for the predetermined pulse time, a laser-induced optical breakdown event occurs in the medium.

11. The method of claim 10, wherein the laser-induced optical breakdown event in the medium is controlled to cause a jet of the medium, which propagates in a direction towards the epithelial tissue layer.

12. The method of claim 11, comprising injecting a portion of the medium into the epithelial tissue layer by means of the jet.

13. The method of claim 10, wherein the step of generating a laser beam and causing a laser-induced optical breakdown event within the medium is repeated a plurality of times.

14. The method of claim 13, wherein the target positions of at least some focal spots differ from each other.

15. The method of claim 10, comprising the further step of applying a topical formulation onto the epithelial tissue layer.

16. The system of claim 1, wherein, in operation, the target position is located at a distance smaller than 3 mm from the surface of the epithelial tissue layer.

17. The system of claim 1, wherein the reservoir has a cup-shape with an open bottom.

18. The method of claim 10, wherein, in operation, the target position is located at a distance smaller than 3 mm from the surface of the epithelial tissue layer.

19. The method of claim 10, wherein, in operation, the target position is located at a distance in a range between 300 and 900 micrometer from the surface of the epithelial tissue layer.

20. The method of claim 10, wherein the reservoir has a cup-shape with an open bottom.

* * * * *